US012415095B2

(12) United States Patent
Kim et al.

(10) Patent No.: US 12,415,095 B2
(45) Date of Patent: Sep. 16, 2025

(54) ULTRASOUND APPARATUS WITH TWO-ROW TRANSFER WAY OF TRANSDUCER

(71) Applicant: VIOL CO., LTD., Seongnam-si (KR)

(72) Inventors: Ju Hwan Kim, Gwangmyeong-si (KR); Sangjin Lee, Anyang-si (KR)

(73) Assignee: VIOL CO., LTD., Seongnam-si (KR)

( * ) Notice: Subject to any disclaimer, the term of this patent is extended or adjusted under 35 U.S.C. 154(b) by 64 days.

(21) Appl. No.: 18/266,065

(22) PCT Filed: Nov. 9, 2021

(86) PCT No.: PCT/KR2021/016254
§ 371 (c)(1),
(2) Date: Jun. 8, 2023

(87) PCT Pub. No.: WO2022/124597
PCT Pub. Date: Jun. 16, 2022

(65) Prior Publication Data
US 2024/0024706 A1 Jan. 25, 2024

(30) Foreign Application Priority Data

Dec. 11, 2020 (KR) .................. 10-2020-0173686
Feb. 19, 2021 (KR) .................. 10-2021-0022788

(51) Int. Cl.
*A61N 7/02* (2006.01)
*A61N 7/00* (2006.01)

(52) U.S. Cl.
CPC ........ *A61N 7/02* (2013.01); *A61N 2007/0034* (2013.01)

(58) Field of Classification Search
CPC .............. A61N 7/02; A61N 2007/0034; A61N 2007/0008; A61N 2007/0091; A61N 7/00;
(Continued)

(56) References Cited

U.S. PATENT DOCUMENTS

| 2005/0187495 A1 | 8/2005 | Quistgaard et al. |
| 2016/0001097 A1 | 1/2016 | Cho et al. |

(Continued)

FOREIGN PATENT DOCUMENTS

| CA | 2726812 | 12/2009 |
| CN | 104367340 | 2/2015 |

(Continued)

OTHER PUBLICATIONS

EPO, Search Report of EP 21903625.8 dated Sep. 26, 2024.
EPO, Search Report of EP 21903644.9 dated Nov. 19, 2024, total 23 pages.

*Primary Examiner* — Hien N Nguyen
(74) *Attorney, Agent, or Firm* — LEX IP MEISTER, PLLC (57) ABSTRACT

An ultrasonic device employing a two-row moving method of a transducer according to the present disclosure, the ultrasonic device including: a cartridge comprising a transducer configured to generate ultrasonic waves; and a moving device configured to move the transducer, in which the moving device includes: a moving main body; a moving block positioned on the moving main body and connected to the transducer and configured to move with the transducer; a first moving part configured to move the moving block along a first direction; and a second moving part configured to move the moving block along a second direction that intersects the first direction.

10 Claims, 8 Drawing Sheets

(58) Field of Classification Search
CPC ...... A61B 2034/2059; A61B 2090/065; A61B 8/00; A61B 8/4427; A61B 8/4209; A61B 8/429; A61B 2017/00876; A61B 2034/2048; A61B 2560/0462; A61B 2562/14

See application file for complete search history.

(56) References Cited

U.S. PATENT DOCUMENTS

| | | | |
|---|---|---|---|
| 2017/0303895 | A1 | 10/2017 | Park et al. |
| 2018/0055478 | A1* | 3/2018 | Choi ................. A61N 7/022 |
| 2019/0366129 | A1* | 12/2019 | Park ..................... A61N 7/02 |

FOREIGN PATENT DOCUMENTS

| | | |
|---|---|---|
| CN | 109853764 | 6/2019 |
| CN | 209364502 | 9/2019 |
| JP | 63-145052 | 9/1988 |
| JP | 2007-516810 | 6/2007 |
| JP | 2018-500075 | 1/2018 |
| JP | 2020-505116 | 2/2020 |
| JP | 2021194537 | 12/2021 |
| KR | 20070029383 | 3/2007 |
| KR | 10-0750719 | 8/2007 |
| KR | 10-1188930 | 10/2012 |
| KR | 10-1191347 | 10/2012 |
| KR | 10-2014-0138030 | 12/2014 |
| KR | 10-2016-0073603 | 6/2016 |
| KR | 20-2016-0002847 | 8/2016 |
| KR | 10-1700334 | 1/2017 |
| KR | 10-2017-0048911 | 5/2017 |
| KR | 101756618 | 7/2017 |
| KR | 10-1793253 | 11/2017 |
| KR | 10-2018-0015095 | 2/2018 |
| KR | 101964257 | 4/2019 |
| KR | 102094444 | 3/2020 |
| KR | 102111103 | 5/2020 |
| KR | 20200085449 | 7/2020 |
| WO | 2014055708 | 4/2014 |
| WO | 2018-143544 | 8/2018 |

\* cited by examiner

FIG. 7

ULTRASOUND APPARATUS WITH TWO-ROW TRANSFER WAY OF TRANSDUCER

TECHNICAL FIELD

The present disclosure relates to an ultrasonic device, and more particularly to an ultrasonic device that uses high-intensity focused ultrasound and employs a two-row moving method of a transducer.

BACKGROUND ART

In recent years, a variety of procedures have been developed for skin aesthetics and obesity treatment, and there has been a growing interest in procedures that are performed by non-invasive method.

Ultrasound has been widely used for non-invasive procedures, and ultrasonic devices that utilize high-intensity focused ultrasound (HIFU) have recently become popular. For example, ultrasound devices are being developed to non-invasively perform cosmetic procedures such as face lifting or skin tightening by directing high-intensity focused ultrasonic waves into the skin tissue, or to non-invasively treat obesity by directing high-intensity focused ultrasonic waves into the subcutaneous fat layer to non-invasively burn, melt, and break down fatty tissue.

The high-intensity focused ultrasound device used in procedures for skin aesthetics includes an image monitor, an ultrasound control unit, and a hand piece, the hand piece being coupled to a cartridge containing a transducer that generates ultrasonic waves.

Since the transducer, which generates the ultrasonic waves, reciprocates in a straight line, these ultrasound devices have a narrow treatment range, which makes the treatment slow. The operator has to move the hand piece frequently to increase the treatment range, which makes the treatment to be cumbersome.

DISCLOSURE

Technical Problem

The present disclosure aims to provide an ultrasonic device that is capable of speeding up treatments and minimizing operator's movements.

Technical Solution

An ultrasonic device employing a two-row moving method of a transducer according to the present disclosure, the ultrasonic device including: a cartridge comprising a transducer configured to generate ultrasonic waves; and a moving device configured to move the transducer, in which the moving device includes: a moving main body; a moving block positioned on the moving main body and connected to the transducer and configured to move with the transducer; a first moving part configured to move the moving block along a first direction; and a second moving part configured to move the moving block along a second direction that intersects the first direction.

The first moving part may include: a moving nut connected to the moving block; a screw part engaged with the moving nut and configured to move the moving block; and a driving motor configured to provide a driving force to the screw part.

The first moving part may further include a pair of guide rods configured to guide the moving block to move along the first direction.

The second moving part may include: a position adjusting part installed on the moving main body and configured to move the moving block along the second direction upon coming into contact with the moving block.

The position adjusting part may include: a lower end position adjusting part coming in contact with a lower end of the moving block; and an upper end position adjusting part coming in contact with an upper end of the moving block.

The second moving part may further include a pair of moving grooves formed in the moving block and allowing the first moving part to move along the second direction.

The guide rod may move to the moving groove when the first moving part moves along the second direction.

The moving block may be installed to be inclined to the first direction.

The cartridge may further include: a cartridge main body having the transducer installed therein; a cartridge block magnetically coupled to the moving block and configured to move with the moving block; and a pair of cartridge guide rods configured to guide the cartridge block to move along the first direction.

The cartridge may further include a cartridge position adjusting part configured to guide the cartridge block to move along the second direction.

The moving device is installed on the moving main body and may further include a motion sensor configured to detect a motion of the moving block.

The cartridge may further include a pressure sensor installed at a lower end of the cartridge and configured to measure pressure applied externally.

Advantageous Effect

The transducer of the ultrasonic device according to an embodiment of the present disclosure may move in the straight section along the first direction, then move along the second direction, and then move along another straight section.

Therefore, the transducer moves along two straight sections and the treatment is performing, thereby allowing for faster and more precise treatments and minimizing the operator's movement because the operator does not need to move the hand piece frequently.

MODE FOR INVENTION

Hereinafter, embodiments of the present disclosure will be described in detail with reference to the accompanying drawings so that those with ordinary skill in the art to which the present disclosure pertains may easily carry out the embodiments. The present disclosure may be implemented in various different ways, and is not limited to the embodiments described herein.

Figure 1:
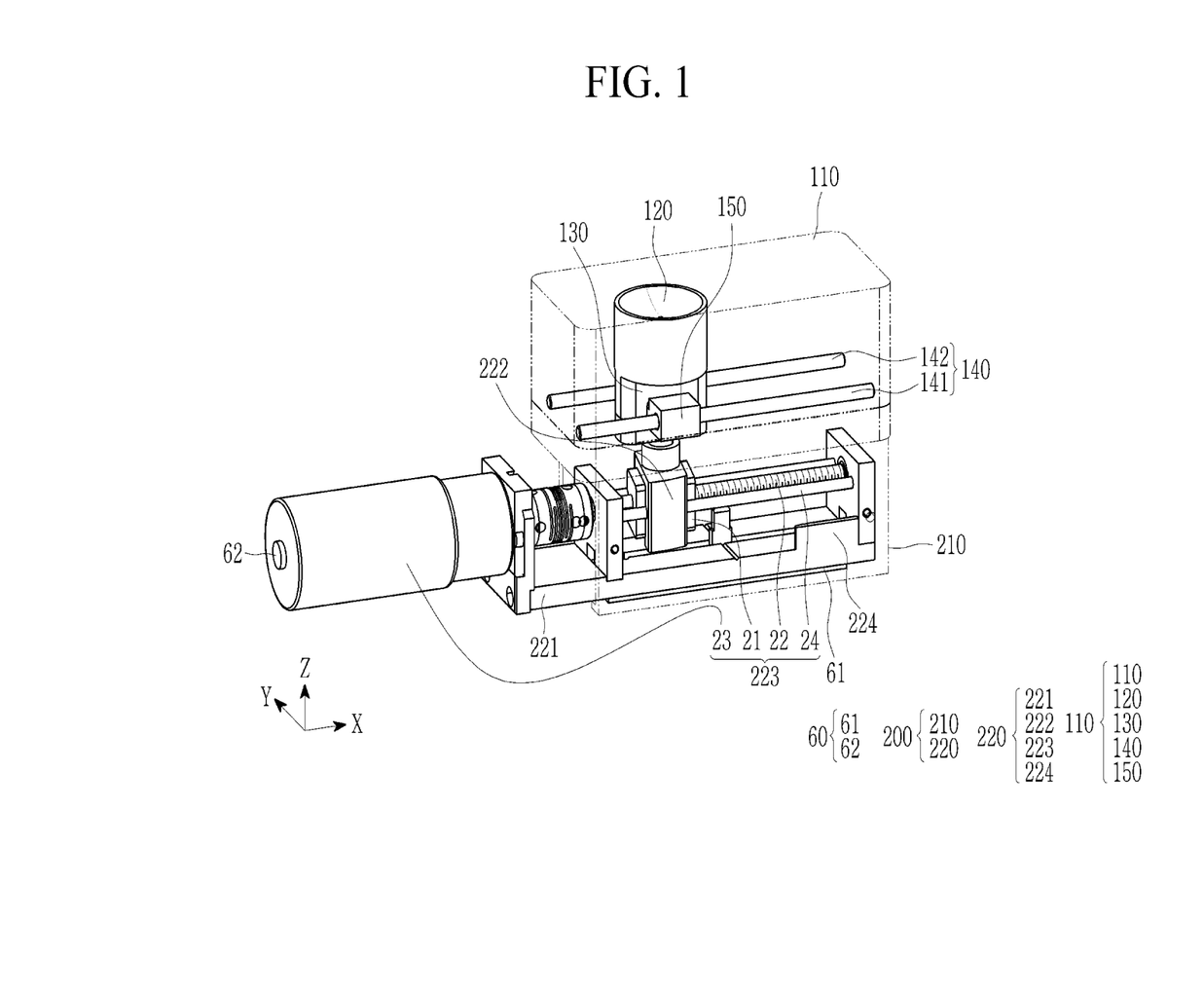
FIG. 1 is a perspective view of an ultrasonic device according to an embodiment of the present disclosure.
Figure 2:
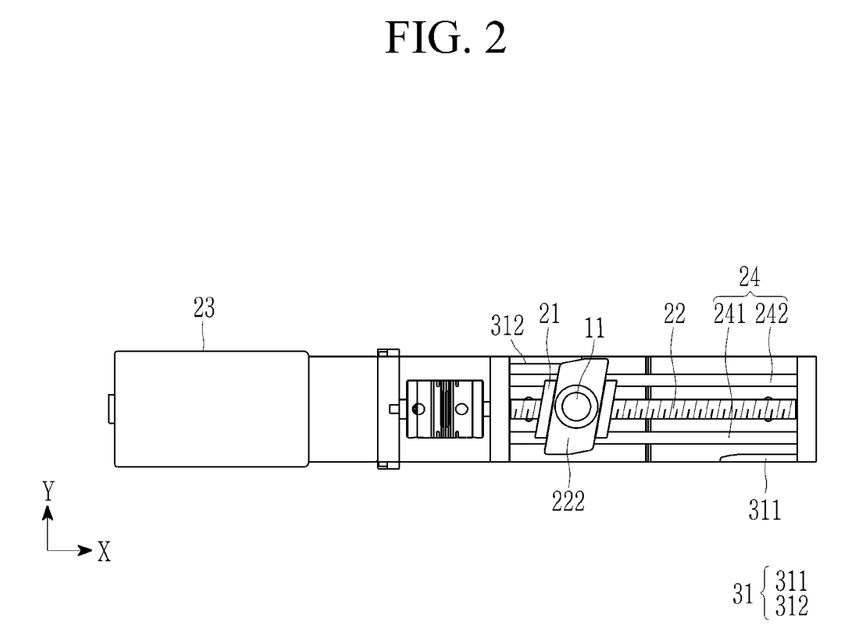
FIG. 2 is a top plan view of a moving device of the ultrasonic device according to an embodiment of the present disclosure.

FIG. 1 is a perspective view of an ultrasonic device according to an embodiment of the present disclosure, and FIG. 2 is a top plan view of a moving device of the ultrasonic device according to an embodiment of the present disclosure.

As illustrated in FIGS. 1 and 2, an ultrasonic device according to an embodiment of the present disclosure includes a cartridge 100 including a transducer 120 that irradiates a person to be treated with HIFU, and a hand piece 200 configured to adjust a treatment range in which the person to be treated is irradiated with HIFU.

The cartridge 100 may include a cartridge main body 110, a transducer 120 that generates ultrasonic waves, a cartridge block 130, a pair of cartridge guide rods 140, and a cartridge position adjusting part 150.

The hand piece 200 may include a hand piece main body 210, and a moving device 220 that is installed within the hand piece main body 210 and moves the transducer 120.

The hand piece body 210 has a roughly cuboidal shape, but is not necessarily limited thereto, and various other shapes are possible.

The moving device 220 may include a moving main body 221, a moving block 222, a first moving part 223, and a second moving part 224.

The moving main body 221 may support the moving block 222, the first moving part 223, and the second moving part 224.

The moving block 222 is positioned on the moving main body 221 and is connected to the transducer 120 so that the moving block 222 may move together with the transducer 120. A first magnetic member 11 may be installed on an upper portion of the moving block 222. The moving block 222 may be installed to be inclined to a first direction X in a plan view. Therefore, even when the moving block 222 is in contact with the position adjusting part 31 of the second moving part 224 and moves in a second direction Y, a rotation or position change of the moving block 222 may be minimized.

The first moving part 223 may allow the moving block 222 to reciprocate along the first direction X.

The first moving part 223 may include a moving nut 21, a screw part 22, a driving motor 23, and a pair of guide rods 24.

The moving nut 21 has a cross-section of a roughly rectangular or parallelogram shape and may be installed inside the moving block 222 to be connected to the moving block 222. The moving nut 21 has a screw thread formed therein, which may be engaged with the screw part 22.

The screw part 22 is engaged with an internal screw thread of the moving nut 21, so that the moving nut 21 may move forward or backward and reciprocate along the first direction X according to a rotation of the screw part 22. In this case, the moving block 222 connected to the moving nut 21 may also move with the moving nut.

The driving motor 23 may provide a driving force to the screw part 22 to rotate the screw part 22, thereby allowing the moving block 222 to move.

Figure 3:
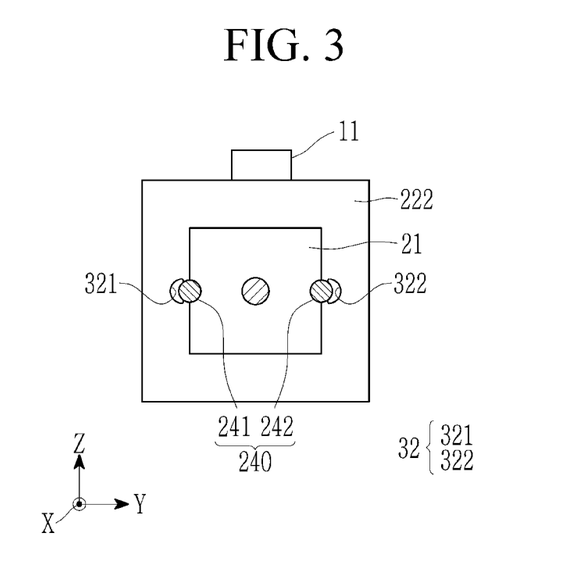
FIG. 3 is a partial front view of the moving apparatus of the ultrasonic device according to an embodiment of the present disclosure.

FIG. 3 is a partial front view of the moving apparatus of the ultrasonic device according to an embodiment of the present disclosure.

As illustrated in FIG. 3, the pair of guide rods 24 simultaneously penetrate the moving nut 21 and the moving block 222 and may guide the moving block 222 to move along the first direction X. That is, the pair of guide rods 24 may be positioned in a semicircle-shaped groove formed in the sidewall of the moving nut 21 and in a semicircle-shaped groove adjacent thereto and formed in the sidewall of the moving block 222. The pair of guide rods 24 may include a first guide rod 241 and a second guide rod 242 positioned on both sides of the screw unit 22, respectively.

The first moving part 223 may further include a position control unit 60 that controls a position of the moving block 222 that moves in the first direction X. The position control unit 60 may include a position determining portion 61 installed on the moving main body 221 corresponding to the screw unit 22, and an encoder 62 installed on the driving motor 23. The position determining portion 61 may include a variable resistor that determines the position of the moving block 222 based on a difference in electrical resistance, or a photo sensor that determines the position of the moving block 222 based on a difference in light intensity.

The second moving part 224 may allow the moving block 222 to move along the second direction Y that intersects the first direction X.

The second moving part 224 may include a position adjusting part 31 and a pair of moving grooves 32.

As illustrated in FIGS. 1 and 2, the position adjusting part 31 is installed on the moving main body 221 and may move the moving block 222 along the second direction Y when in contact with the moving block 222.

The position adjusting part 31 may include a lower end position adjusting part 311 installed on one side of a lower portion of the moving main body 221 and capable of being in contact with the lower end of the moving block 222, and an upper end position adjusting part 312 installed on the other side of an upper portion of the moving main body 221 and capable of being in contact with the upper end of the moving block 222.

In this case, as illustrated in FIG. 3, the pair of moving grooves 32 may include a first moving groove 321 and a second moving groove 322 spaced apart from each other and formed in the moving block 222. The first moving groove 321 may be formed adjacent to the first guide rod 241, and the second moving groove 322 may be formed adjacent to the second guide rod 242. This pair of moving grooves 32 allows the first moving part 223 to move along the second direction Y. For example, when the moving block 222 moves to a right side along the first direction X and comes into contact with the lower end position adjusting part 311, which is positioned at a lower right side, the second guide rod 242 moves to the second moving groove 322, so that the moving block 222 may move upward along the second direction Y without much resistance. In addition, when the moving block 222 moves to a left side along the first direction X and comes into contact with the upper end position adjusting part 312, which is positioned at an upper left side, the first guide rod 241 moves to the first moving groove 321, so that the moving block 222 may move downward along the second direction Y without much resistance.

Figure 4:
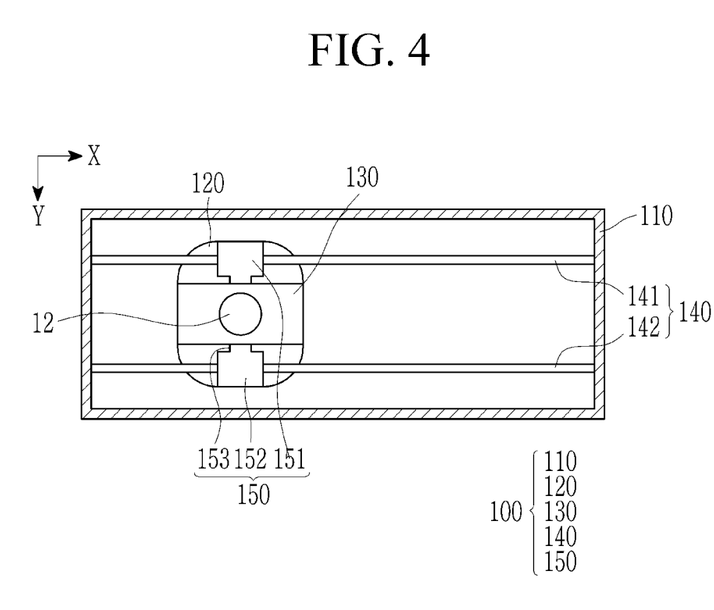
FIG. 4 is a bottom plan view of a cartridge of the ultrasonic device according to an embodiment of the present disclosure.
Figure 5:
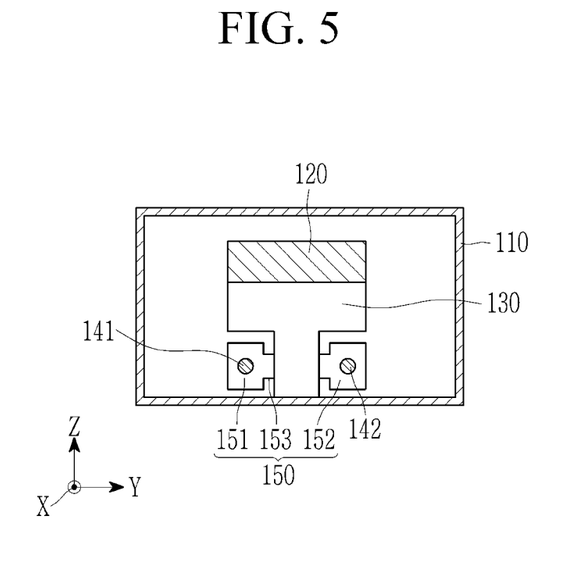
FIG. 5 is a front view of the cartridge of the ultrasonic device according to an embodiment of the present disclosure.

FIG. 4 is a bottom plan view of a cartridge of the ultrasonic device according to an embodiment of the present disclosure, and FIG. 5 is a front view of the cartridge of the ultrasonic device according to an embodiment of the present disclosure.

As illustrated in FIGS. 1, 4, and 5, the transducer 120 may be installed inside the cartridge main body 110.

The transducer 120 may irradiate and treat the person to be treated with HIFU.

The cartridge block 130 is magnetically coupled to the moving block 222 and may move with the moving block 222. In a lower portion of the cartridge block 130, a second magnetic member 12 may be installed that is magnetically coupled to the first magnetic member 11 installed in the upper portion of the moving block 222.

The pair of cartridge guide rods 140 may guide the cartridge block 130 to move along the first direction X. The pair of cartridge guide rods 140 may include a first cartridge guide rod 141 and a second cartridge guide rod 142 positioned on either side with respect to the cartridge block 130. The pair of cartridge guide rods 140 may penetrate the cartridge position adjusting part 150.

The cartridge position adjusting part 150 may guide the cartridge block 130 to move along the second direction Y. The cartridge position adjusting part 150 may include a first main member 151 connected to the first cartridge guide rod 141, a second main member 152 connected to the second cartridge guide rod 142, and a connection member 153 connecting the first main member 151 and the second main member 152 to each other.

When the moving block 222 moves along the second direction Y, the cartridge block 130 magnetically coupled to the moving block 222 may also move along the second direction Y through the connection member 53, so that the transducer 120 connected to the cartridge block 130 may move along the second direction Y without much resistance.

FIGS. 6A to 6F are top plan views sequentially illustrating how the moving block of the ultrasonic device moves in two straight sections according to an embodiment of the present disclosure.

Figure 6A:
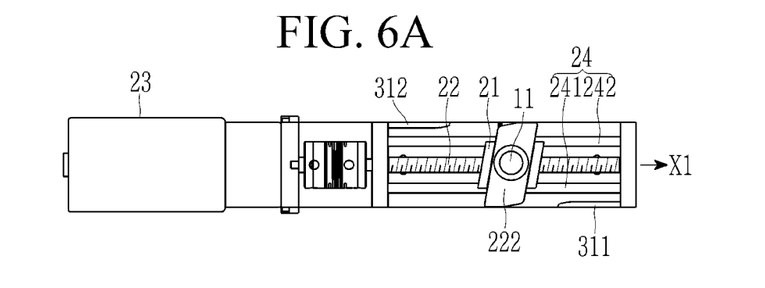
FIGS. 6A to 6F are top plan views sequentially illustrating how the moving block of the ultrasonic device moves in two straight sections according to an embodiment of the present disclosure.
Figure 6B:
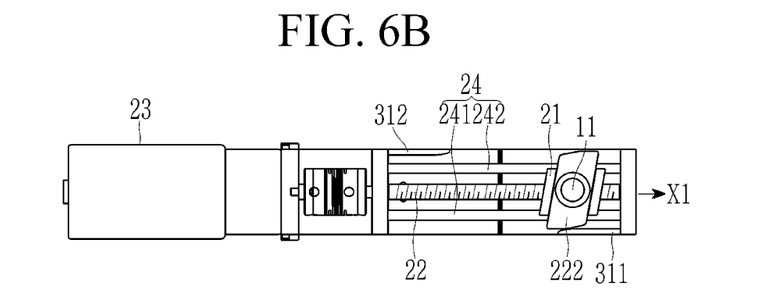

As illustrated in FIG. 6A, the moving block 222 moves to the right side along the first direction X1 and comes into contact with the lower end position adjusting part 311, which is positioned at a lower right side, as illustrated in FIG. 6B. In this case, the transducer 120 that moves with the moving block 222 moves in a straight section to a right side along the first direction X1.

Figure 6C:
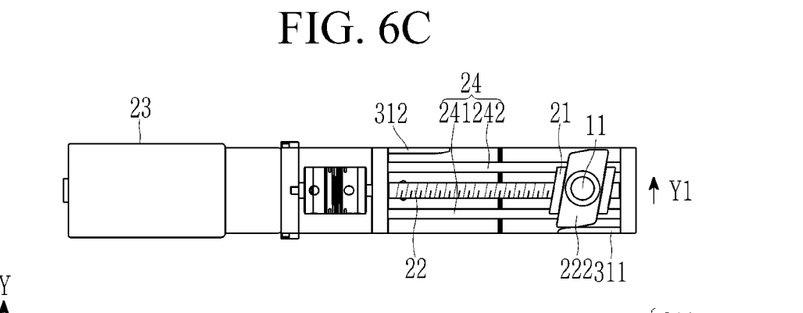

Next, as illustrated in FIG. 6C, the moving block 222, which is continuously moved by the screw part 22, is pushed by the lower end position adjusting part 311 to move upward along the second direction Y1.

Figure 6D:
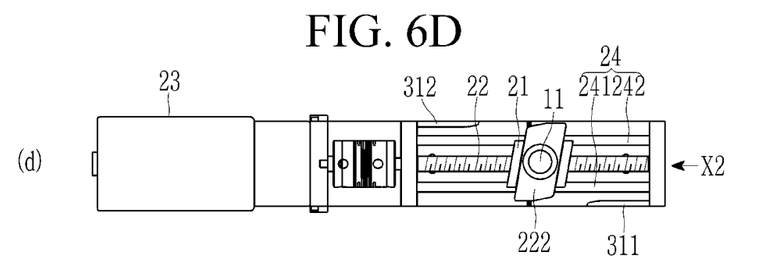
Figure 6E:
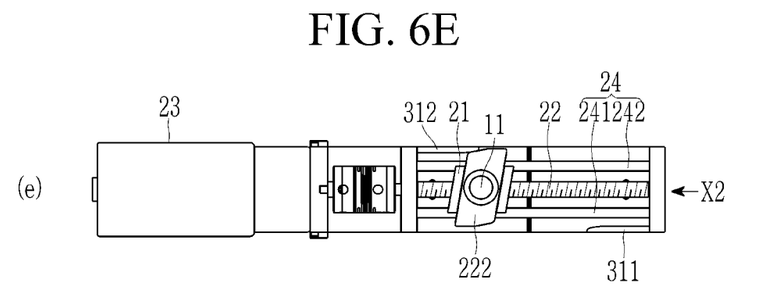

Next, as illustrated in FIG. 6D, the moving block 222 moves to a left side along the first direction X2, and comes into contact with the upper end position adjusting part 312, which is positioned to an upper left side, as illustrated in FIG. 6E. In this case, the transducer 120 that moves with the moving block 222 moves to another straight section to a left side along the first direction X2.

Figure 6F:
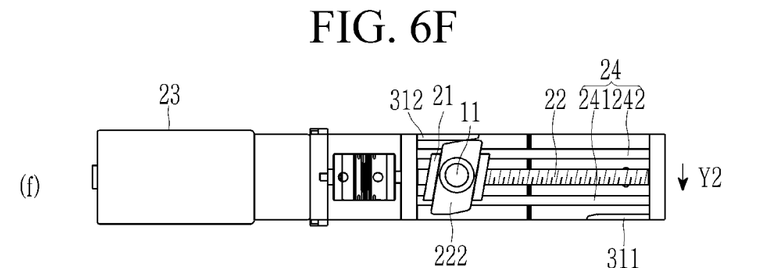

Next, as illustrated in FIG. 6F, the moving block 222, which is continuously moved by the screw part 22, is pushed by the upper end position adjusting part 312 to move downward along the second direction Y2.

As described above, the transducer of the ultrasonic device according to an embodiment of the present disclosure may move in the straight section along the first direction X, then move along the second direction Y, and then move along another straight section. Therefore, since the transducer moves along two straight sections and the treatment is performing, the operator does not need to move the hand piece frequently to move to the next treatment area. Therefore, more evenly spaced and precise treatments are possible.

Meanwhile, other embodiments of the ultrasonic device of the present disclosure are possible in which a motion sensor and a pressure sensor are added.

Hereinafter, with reference to FIG. 7, an ultrasonic device according to another embodiment of the present disclosure will be described in detail.

Figure 7:
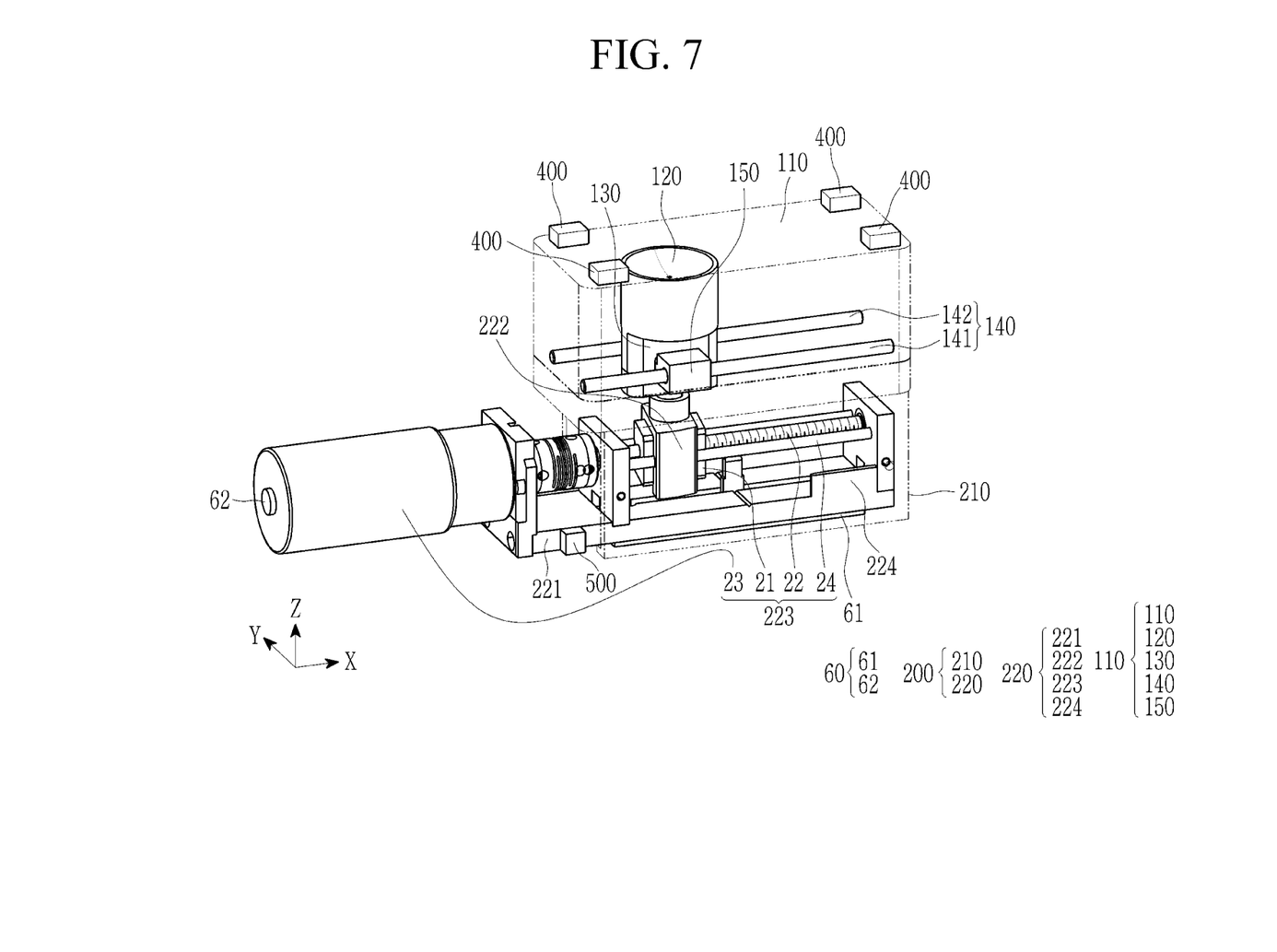
FIG. 7 is a perspective view of an ultrasonic device according to another embodiment of the present disclosure.

FIG. 7 is a perspective view of an ultrasonic device according to another embodiment of the present disclosure.

Another embodiment illustrated in FIG. 7 is substantially the same as an embodiment illustrated in FIGS. 1 to 5, except for the motion sensor and the pressure sensor, and repetitive descriptions will be omitted.

As illustrated in FIG. 7, a cartridge of an ultrasonic device according to another embodiment of the present disclosure may include the cartridge main body 110, the transducer 120 that generates ultrasonic waves, the cartridge block 130, the pair of cartridge guide rods 140, the cartridge position adjusting part 150, and a pressure sensor 400.

The pressure sensor 400 may be installed at a lower end of the cartridge 100, that is, at a lower end of the cartridge main body 110, to measure externally applied pressure.

Here, the pressure sensor 400 may be positioned at a suitable position on a lower end surface of the cartridge 100 to effectively measure pressure on a skin contact surface when the lower end of the cartridge 100 is in contact with the skin. For example, when the pressure sensor is positioned at each corner of a lower end surface of the cartridge, pressure may be effectively measured as the pressure sensor comes into contact with the skin contact surface.

Ultrasound devices in the related art have a treatment depth of 1 to 5 mm, depending on a position of the transducer inside the cartridge. However, because depth of the treatment may be deeper or shallower, depending on pressure by which an operator presses the cartridge with the hand piece against a treatment area, the depth of the treatment becomes inconsistent since the treatment effectiveness is determined by the operator's skill level.

However, by installing the pressure sensor 400 at the lower end of the cartridge 100, the ultrasonic device according to the present embodiment may measure the pressure of the hand piece applied to the treatment area and, when the correct pressure is applied, may use light or sound to make the operator recognize the pressure of the hand piece. Therefore, the same treatment effect may be achieved regardless of the operator's skill level.

In addition, the moving device 220 of the ultrasonic device according to another embodiment of the present disclosure may include the moving main body 221, the moving block 222, the first moving part 223, the second moving part 224, and a motion sensor 500.

The motion sensor 500 is installed on the moving main body 221 and may detect a motion of the moving block 222.

In ultrasound devices in the related art, the operator moves the hand piece to navigate the treatment area to apply ultrasound to multiple treatment areas, but the movement to the treatment area cannot be accurately verified, so when the cartridge is not accurately moved to the treatment area, heat may be applied to the same area again, causing necrosis of the skin in the treatment area.

However, by installing the motion sensor 500 on the moving main body 221 of the hand piece 200, the ultrasound device according to the present embodiment may perform the ultrasound irradiation again when the movement to the treatment area is confirmed after the motion of the moving block 222 is detected. That is, after the treatment position of the moving block 222 is confirmed by the motion sensor 500, light or sound may be used to help the operator confirm an exact position of the treatment area. Therefore, the operator does not need to identify the position of the ultrasound irradiation each time, and even when the ultrasonic device is operated in continuous mode, heat is not applied to the same treatment area, which can prevent necrosis of the skin in the treatment area.

The motion sensors 500 may include a gyro sensor, an accelerometer, a geomagnetic sensor, or the like.

While the present disclosure has been described with reference to the aforementioned exemplary embodiments, the person skilled in the art will easily understand that the present disclosure is not limited to the disclosed exemplary embodiments, but can be variously corrected and modified without departing from the scope of the appended claims.

The invention claimed is:

1. An ultrasonic device comprising:
a cartridge comprising a transducer configured to generate ultrasonic waves; and
a moving device configured to move the transducer,
wherein the moving device comprises:
a moving main body;
a moving block positioned on the moving main body and connected to the transducer and configured to move with the transducer;
a first moving part configured to move the moving block along a first direction; and
a second moving part configured to move the moving block along a second direction that intersects the first direction,
wherein the moving block is installed to be inclined to the first direction in a plane view,
the first moving part comprises a moving nut connected to the moving block, and a screw part engaged with the moving nut and configured to move the moving block, and
the moving nut is installed on the screw part with a same inclination angle as the moving block.

2. The ultrasonic device of claim 1, wherein:
the first moving part further comprises:
a driving motor configured to provide a driving force to the screw part.

3. The ultrasonic device of claim 2, wherein:
the first moving part further comprises a pair of guide rods configured to guide the moving block to move along the first direction.

4. The ultrasonic device of claim 1, wherein:
the second moving part comprises: a position adjusting part installed on the moving main body and configured to move the moving block along the second direction upon coming into contact with the moving block.

5. The ultrasonic device of claim 4, wherein:
the position adjusting part comprises:
a lower end position adjusting part coming in contact with a lower end of the moving block; and
an upper end position adjusting part coming in contact with an upper end of the moving block.

6. The ultrasonic device of claim 4, wherein:
the second moving part further comprises a pair of moving grooves formed in the moving block and the moving block with the moving grooves that allow the moving block to move along the second direction.

7. The ultrasonic device of claim 1, wherein:
the cartridge further comprises:
a cartridge main body having the transducer installed therein;
a cartridge block magnetically coupled to the moving block and configured to move with the moving block; and
a pair of cartridge guide rods configured to guide the cartridge block to move along the first direction.

8. The ultrasonic device of claim 7, wherein:
the cartridge further comprises a cartridge position adjusting part configured to guide the cartridge block to move along the second direction.

9. The ultrasonic device of claim 1, wherein:
the moving device further comprises a motion sensor installed on the moving main body and configured to detect a motion of the moving block.

10. The ultrasonic device of claim 1, wherein:
the cartridge further comprises a pressure sensor installed at a lower end of the cartridge and configured to measure pressure applied externally.

* * * * *